(12) United States Patent
Saxena (10) Patent No.: US 8,921,516 B2
(45) Date of Patent: Dec. 30, 2014

(54) SYNTHETIC, DEFINED FIBRONECTIN MIMETIC PEPTIDES AND SURFACES MODIFIED WITH THE SAME

(75) Inventor: Deepa Saxena, Framingham, MA (US)

(73) Assignee: Corning Incorporated, Corning, NY (US)

( * ) Notice: Subject to any disclaimer, the term of this patent is extended or adjusted under 35 U.S.C. 154(b) by 130 days.

(21) Appl. No.: 13/309,756

(22) Filed: Dec. 2, 2011

(65) Prior Publication Data

US 2012/0149871 A1 Jun. 14, 2012

Related U.S. Application Data

(60) Provisional application No. 61/420,818, filed on Dec. 8, 2010.

(51) Int. Cl.
*C07K 14/78* (2006.01)
*C12N 5/00* (2006.01)
*A61L 27/34* (2006.01)

(52) U.S. Cl.
CPC .............. *C07K 14/78* (2013.01); *C12N 5/0068* (2013.01); *A61L 27/34* (2013.01); *C12N 2533/52* (2013.01)
USPC ......................................................... 530/324

(58) Field of Classification Search
CPC ......... A61K 38/00; A61K 30/08; C07K 14/78
See application file for complete search history.

(56) References Cited

U.S. PATENT DOCUMENTS

| 5,171,318 A | 12/1992 | Gibson et al. |
| 2002/0068047 A1 * | 6/2002 | Livant .......................... 424/93.7 |

FOREIGN PATENT DOCUMENTS

| WO | 89/01942 A1 | 3/1989 |
| WO | 92/09200 A1 | 6/1992 |
| WO | WO 2008008523 A1 * | 1/2008 |

OTHER PUBLICATIONS

Extended European Search Report EP 11 19 1960 mailed Mar. 26, 2012.
Wang et al.; Fibronectin's Central Cell-binding Domain Supports Focal Adhesion Formation and Rho Signal Transduction; The Journal of Biological Chemistry; Aug. 5, 2005; vol. 280, No. 31; pp. 28803-28810.
Cutler and Garcia, Biomaterials, 24:1759-1770 (2003).

* cited by examiner

*Primary Examiner* — Karlheinz R Skowronek
*Assistant Examiner* — Lianko Garyu
(74) *Attorney, Agent, or Firm* — Hoffmann & Baron, LLP (57) ABSTRACT

The present invention discloses compositions for applications that mimic fibronectin coated surfaces. Advantageously, such compositions provide an animal free (xeno-free, and human-component-free), synthetic, chemically defined surface that mimics at least one of the functionalities of fibronectin.

8 Claims, 5 Drawing Sheets

SYNTHETIC, DEFINED FIBRONECTIN MIMETIC PEPTIDES AND SURFACES MODIFIED WITH THE SAME

CROSS-REFERENCE TO RELATED APPLICATION

This application claims the benefit of U.S. Provisional Application No. 61/420,818, filed Dec. 8, 2010, the contents of which is incorporated by reference herein.

FIELD OF THE INVENTION

The present invention relates to compounds and surfaces modified therewith which mimic one or more functional characteristics of fibronectin. More particularly, the present invention relates to xeno-free, human or animal-component-free, synthetic, chemically defined compounds and surfaces modified therewith which provide comparable cell attachment to a coating of human fibronectin.

BACKGROUND OF THE INVENTION

Extracellular matrix (ECM) protein coated surfaces have been widely used in cell culture and coating implanting devices. In particular, fibronectin is a commonly used ECM protein used in cell culture that supports cell attachment, growth, migration and differentiation. ECM proteins used for coating surfaces for cell culture are generally of human or other animal origin and often poorly defined. The use of such ECM proteins can be problematic, for example, in human therapeutic applications. Although isolated human ECM proteins can be used for coating such surfaces, the cost associated with some of the ECMs therewith is very high. Additionally, as with recombinant human ECM proteins, variability in cell culture may result from different batches of isolated ECM protein due to variability in the contaminants present therein. Furthermore, variability in cell culture may arise from the self-coating process itself which is generally employed for both isolated and recombinant fibronectin. Thus, there is a need for xeno-free, human or animal-component-free, synthetic, chemically defined surfaces that mimic fibronectin coated surfaces.

SUMMARY OF THE INVENTION

The present invention provides compounds and surfaces modified with the same that are xeno-free, human or animal-component-free, synthetic and chemically defined. Advantageously, surfaces modified with such compounds mimic a human fibronectin coated surface. Furthermore, such xeno-free, human or animal-component-free, synthetic and chemically defined coatings avoid the issues associated with animal-derived products which are poorly defined and may also elicit an immune response in therapeutic applications. Further, the present invention provides cell culture vessels including a surface modified with a compound in accordance with the present invention.

In one aspect, the present invention provides compounds including at least two regions of a fibronectin cell-binding domain joined by a flexible linker wherein at least one region includes amino acid sequence GRGDSP (SEQ ID NO: 1) and another region includes $X_1X_2X_3X_4X_5X_6X_7X_8X_9X_{10}X_{11}X_{12}X_{13}RX_{15}PX_{17}SRNX_{21}X_{22}TLTX_{26}$ (SEQ ID NO: 2) wherein $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, V, A, G or is absent, $X_8$ denotes G, A or is absent, $X_9$ denotes R or G, $X_{10}$ denotes P, A, Q or G, $X_{11}$ denotes R or K, $X_{12}$ denotes E, Q, W, A or G, $X_{13}$ denotes D or E, $X_{15}$ denotes V, L or I, $X_{17}$ denotes H or P, $X_{21}$ denotes S, T or G, $X_{22}$ denotes I or L and $X_{26}$ denotes N or H.

In one embodiment, $X_7$ denotes S. In one embodiment, $X_8$ denotes G. In one embodiment, $X_9$ denotes R. In one embodiment, $X_{10}$ denotes G or A. In one embodiment, $X_{11}$ denotes R. In one embodiment, $X_{12}$ denotes E, A or G. In one embodiment, $X_{13}$ denotes D. In one embodiment, $X_{15}$ denotes V. In one embodiment, $X_{17}$ denotes H. In one embodiment, $X_{22}$ denotes I. In one embodiment, $X_{26}$ denotes N.

In one embodiment, $X_7$ denotes S and $X_8$ denotes G. In one embodiment, $X_7$ denotes S, $X_8$ denotes G and $X_9$ denotes R. In one embodiment, $X_7$ denotes S, $X_8$ denotes G, $X_9$ denotes R and $X_{10}$ denotes G or A. In one embodiment, $X_7$ denotes S, $X_8$ denotes G, $X_9$ denotes R, $X_{10}$ denotes G or A and $X_{11}$ denotes R. In one embodiment, $X_7$ denotes S, $X_8$ denotes G, $X_9$ denotes R, $X_{10}$ denotes G or A, $X_{11}$ denotes R and $X_{12}$ denotes E, A or G. In one embodiment, $X_7$ denotes S, $X_8$ denotes G, $X_9$ denotes R, $X_{10}$ denotes G or A, $X_{11}$ denotes R, $X_{12}$ denotes E, A or G and $X_{13}$ denotes D. In one embodiment, $X_7$ denotes S, $X_8$ denotes G, $X_9$ denotes R, $X_{10}$ denotes G or A, $X_{11}$ denotes R, $X_{12}$ denotes E, A or G, $X_{13}$ denotes D and $X_{15}$ denotes V. In one embodiment, $X_7$ denotes S, $X_8$ denotes G, $X_9$ denotes R, $X_{10}$ denotes G or A, $X_{11}$ denotes R, $X_{12}$ denotes E, A or G, $X_{13}$ denotes D, $X_{15}$ denotes V and $X_{17}$ denotes H. In one embodiment, $X_7$ denotes S, $X_8$ denotes G, $X_9$ denotes R, $X_{10}$ denotes G or A, $X_{11}$ denotes R, $X_{12}$ denotes E, A or G, $X_{13}$ denotes D, $X_{15}$ denotes V, $X_{17}$ denotes H and $X_{22}$ denotes I. In one embodiment, $X_7$ denotes S, $X_8$ denotes G, $X_9$ denotes R, $X_{10}$ denotes G or A, $X_{11}$ denotes R, $X_{12}$ denotes E, A or G, $X_{13}$ denotes D, $X_{15}$ denotes V, $X_{17}$ denotes H, $X_{22}$ denotes I and $X_{26}$ denotes N.

In one embodiment, the flexible linker includes amino acid sequence SGSGSGSGS (SEQ ID NO: 3), GGSGGSGGS (SEQ ID NO: 4), SGTGSGTGS (SEQ ID NO: 5) or GGGSGGGSGG (SEQ ID NO: 6).

In one embodiment, $X_7$ denotes S; $X_8$ denotes G; $X_9$ denotes R; $X_{10}$ denotes G or A; $X_{11}$ denotes R; $X_{12}$ denotes E, A or G; $X_{13}$ denotes D; $X_{15}$ denotes V; $X_{17}$ denotes H; $X_{22}$ denotes I; $X_{26}$ denotes N and the flexible linker includes amino acid sequence SGSGSGSGS (SEQ ID NO: 3), GGSGGSGGS (SEQ ID NO: 4), SGTGSGTGS (SEQ ID NO: 5) or GGGSGGGSGG (SEQ ID NO: 6).

In another aspect, provided are surfaces wherein at least a portion of the surface includes a coating thereon of a compound having at least two regions of a fibronectin cell-binding domain joined by a flexible linker wherein at least one region includes amino acid sequence GRGDSP (SEQ ID NO: 1) and another region includes $X_1X_2X_3X_4X_5X_6X_7X_8X_9X_{10}X_{11}X_{12}X_{13}RX_{15}PX_{17}SRNX_{21}X_{22}TLTX_{26}$ (SEQ ID NO: 2) wherein $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, V, A, G or is absent, $X_8$ denotes G, A or is absent, $X_9$ denotes R or G, $X_{10}$ denotes P, A, Q or G, $X_{11}$ denotes R or K, $X_{12}$ denotes E, Q, W, A or G, $X_{13}$ denotes D or E, $X_{15}$ denotes V, L or I, $X_{17}$ denotes H or P, $X_{21}$ denotes S, T or G, $X_{22}$ denotes I or L and $X_{26}$ denotes N or H. In one embodiment, the surface mimics one or more functional characteristics of a fibronectin coated surface. In one embodiment, at least a portion of the surface includes a coating thereon wherein $X_7$ denotes S; $X_8$ denotes G; $X_9$ denotes R; $X_{10}$ denotes G or A; $X_{11}$ denotes R; $X_{12}$ denotes E, A or G; $X_{13}$ denotes D; $X_{15}$ denotes V; $X_{17}$ denotes H; $X_{22}$ denotes I and $X_{26}$ denotes N and the flexible linker includes amino acid sequence SGSGSGSGS (SEQ ID NO: 3), GGSGGSGGS (SEQ ID NO: 4), SGTGSGTGS (SEQ ID NO: 5) or GGGSGGGSGG (SEQ ID NO: 6).

In yet another aspect, provided are compositions including a surface wherein at least a portion of the surface includes a coating thereon of a compound having at least two regions of a fibronectin cell-binding domain joined by a flexible linker wherein at least one region includes amino acid sequence GRGDSP (SEQ ID NO: 1) and another region includes $X_1X_2X_3X_4X_5X_6X_7X_8X_9X_{10}X_{11}X_{12}X_{13}RX_{15}PX_{17}SRNX_{21}X_{22}TLTX_{26}$ (SEQ ID NO: 2) wherein $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, V, A, G or is absent, $X_8$ denotes G, A or is absent, $X_9$ denotes R or G, $X_{10}$ denotes P, A, Q or G, $X_{11}$ denotes R or K, $X_{12}$ denotes E, Q, W, A or G, $X_{13}$ denotes D or E, $X_{15}$ denotes V, L or I, $X_{17}$ denotes H or P, $X_{21}$ denotes S, T or G, $X_{22}$ denotes I or L and $X_{26}$ denotes N or H wherein the surface mimics one or more functional characteristics of a fibronectin coated surface.

These and other features of the invention will be better understood through a study of the following detailed description.

BRIEF DESCRIPTION OF THE FIGURES

FIG. 4B illustrates a graph based on quantitative analysis of A-172 human glioblastoma cancer cell attachment by MTS assay to a surface that has a coating thereon of KSGRPREDRVPHSRNSITLTNSGTGSGTGSGRGDSP (SEQ ID NO: 8) referred to therein as "DA2", KSGRPREDRVPHSRNSITLTNGGGSGGGSGGGRGDSP (SEQ ID NO: 9) referred to therein as "DA4", KSGRARADRVPHSRNTITLTNSGSGSGSGSGRGDSP (SEQ ID NO: 10) referred to therein as "DA1", KSGRARADRVPHSRNTITLTNGGSGGSGGSGRGDSP (SEQ ID NO: 11) referred to therein as "DA3", KSGRGRGDRVPHSRNGITLTNSGSGSGSGSGRGDSP (SEQ ID NO: 12) referred to therein as "DA5", KSGRPREDRVPHSRNSITLTNSGSGSGSGSGRGDSP (SEQ ID NO: 7) referred to therein as "Mimetic Peptide", a BD BioCoat fibronectin surface referred to therein as "Fibronectin" or a surface without a peptide coating referred to therein as "No peptide." Notably, the flexible linker is underlined.

DETAILED DESCRIPTION OF THE INVENTION

As used herein the following terms shall have the definitions set forth below.

As used herein, the term "fibronectin cell-binding domain" refers to a region of fibronectin protein derived from human or other animal that is characterized by cell-binding thereto. Exemplary regions of a fibronectin cell-binding domains include, but are not limited to, SGRPREDRVPHSRNSITLTN (SEQ ID NO: 13) and GRGDSP (SEQ ID NO: 1).

As used herein, the phrase "one or more functional characteristics of a fibronectin coated surface" includes, but is not limited to, cell attachment, growth, migration and differentiation of a fibronectin-dependent cell type. Exemplary fibronectin-dependent cell types include, but are not limited to, LNCAP, MIA-Paca-2, A-172 and RKO cells. In one embodiment, one or more functional characteristics of a fibronectin coated surface is characterized using LNCaP cells. In another embodiment, one or more functional characteristics of a fibronectin coated surface is characterized using MIA-PaCa-2 cells. In yet another embodiment, one or more functional characteristics of a fibronectin coated surface is characterized using A-172 cells. In still yet another embodiment, one or more functional characteristics of a fibronectin coated surface is characterized using RKO cells. Desirably, the surface mimics cell attachment of a fibronectin coated surface.

As used herein, the terms "mimic" and "mimics" with regard to the comparison of a cell culture surface coated with a compound of the present invention with a cell culture surface coated with fibronectin refers to the relative similarity in one or more functional characteristics being assessed. Desirably, quantification thereof would reveal at least 90% similarity in at least one functional characteristic.

As used herein, the phrase "flexible linker" refers to a chemical compound that functions to connect two regions of amino acid sequence together in a manner that provides relative flexibility of the joined regions thereby allowing movement thereof. For example, torsion angle changes in a flexible linker allow the regions bound thereto to pivot). In the present invention, a flexible linker is used to join two regions of a fibronectin cell-binding domain together. Though linkers may impact the conformation of the amino acid sequences linked together and consequently, the resultant activity of the overall compound, generally, linkers are not considered to have biological activity in and of themselves. Rather linkers are designed to support the function of the amino acid sequences being joined. Linkers are produced either via recombinant techniques or synthetic techniques (e.g., solid phase synthesis) and may include naturally occurring amino acids, non-naturally occurring amino acids and/or peptidomimetics. Typically, linkers are between 1-15 amino acids in chain length. In certain embodiments, linkers are between 5-10 amino acids in chain length. Linkers are well known in the art and described in numerous publications including, but not limited to, Freund et al., FEBS 320:97-100 (1993); Gururaja et al., *J Pept Res,* 61:163-176 (2003) (linkers GSGS (SEQ ID NO: 14) and GSGSGSGSGS (SEQ ID NO: 15)); Prehoda et al., *Science,* 290:801-806 (2000), Wriggers et al., *Biopolymers,* 80(6):736-746 (2005); and Hu et al., *J Biotechnol,* 107(1):83-90 (2004), Mardilovich et al., *Langmuir,* 22:3259-3264 (2006); Margeta et al., *Proc Natl Acad Science,* 106: 1632-37 (2009) (linker GSGSGSGSGS SEQ ID NO: 15), van Dongen et al., *J Am Chem Soc,* 129:3494-3495 (2007) (linkers containing 2-9 GGSGGS (SEQ ID NO: 16) repeats).

Suitable flexible linkers for use in the present invention include, but are not limited to, SGSGSGSGS (SEQ ID NO: 3), GGSGGSGGS (SEQ ID NO: 4), SGTGSGTGS (SEQ ID NO: 5), and GGGSGGGSGG (SEQ ID NO: 6).

Fibronectin is a high-molecular weight (~440 kDa) ECM glycoprotein that binds to membrane-spanning receptor proteins called integrins as well as ECM components collagen, fibrin and heparan sulfate proteoglycans (e.g., syndecans). Fibronectin supports cell attachment, growth, migration and differentiation and has been shown to play a key role in wound healing, embryonic development and certain types of carcinogenesis.

Structurally, fibronectin exists as a dimer, consisting of two nearly identical polypeptide chains linked by a pair of C-terminal disulfide bonds. Each fibronectin monomer has a molecular weight of 230-250 kDa and contains three types of modules: type I, II, and III. The modules are arranged into several functional and protein-binding domains along the length of a fibronectin monomer. There are four fibronectin-binding domains, allowing fibronectin to associate with other fibronectin molecules. One of these fibronectin-binding domains, $I_{1-5}$, is referred to as the "assembly domain", and it is required for the initiation of fibronectin matrix assembly. Modules $III_{9-10}$ correspond to the "cell-binding domain" of fibronectin. The RGD sequence (Arg-Gly-Asp) is located in $III_{10}$ and is the site of cell attachment via α5β1 and αVβ3 integrins on the cell surface. The "synergy site" is in $III_9$ and has a role in modulating fibronectin's association with α5β1 integrins. Fibronectin also contains domains for fibrin-binding ($I_{1-5}$, $I_{10-12}$), collagen-binding ($I_{6-9}$), fibulin-1-binding ($III_{13-14}$), heparin-binding and syndecan-binding ($III_{12-14}$).

Though not meant to be limited by any theory with the subject invention, the compounds of the present invention include at least two regions of a fibronectin cell-binding domain joined by a flexible linker. The regions are believed to interact with one another in a manner that mimics one or more functional characteristics of fibronectin. In particular, surfaces coated with such compounds mimic cell attachment of a fibronectin coated surface.

The compounds of the present invention may be produced using conventional recombinant technologies or synthetic techniques (e.g., solid phase synthesis). Similarly, such compounds may be purified using conventional techniques to a degree suitable for a given application. Advantageously, synthetic synthesis of compounds of the present invention can provide a level of purity that is at least 70% or greater. In one embodiment, the compounds have a level of purity that is at least 90%. Desirably, compounds of the present invention have a level of purity that is 90% or greater. In certain applications, such as therapeutics, it is particularly preferred that the compounds are synthesized.

Compounds of the present invention include at least two regions of a fibronectin cell-binding domain joined by a flexible linker. Desirably, the compounds of the present invention are less than 100 amino acids long. In certain embodiments, the compounds of the present invention are between about 25 and about 50 amino acids in chain length. The compounds of the present invention may include naturally occurring amino acids, non-naturally occurring amino acids and/or peptidomimetics.

It is understood that one of skill in the art could substitute one or more amino acids of the amino acid sequences described herein for the regions of fibronectin cell-binding domain and/or linker without compromising the ability of the resultant compound when coated on a surface for cell culture to mimic one or more functional properties of a fibronectin coated surface.

In particular, compounds of the present invention may have conservative substitution of one or more amino acids as compared to the naturally occurring fibronectin cell-binding domain. A conservative substitution being defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysine, arginine, histidine), acidic side chains (aspartic acid, glutamic acid), uncharged polar side chains (glycine, asparagine, glutamine, serine, threonine, tyrosine, cysteine), non-polar side chains (alanine, valine, leucine, isoleucine, proline, phenylalanine, methionine, tryptophan), beta-branched side chains (threonine, valine, isoleucine) and aromatic side chains (tyrosine, phenylalanine, tryptophane, histidine).

The present invention provides compounds including at least two regions of a fibronectin cell-binding domain joined by a flexible linker wherein at least one region includes amino acid sequence GRGDSP (SEQ ID NO: 1) and another region includes $X_1X_2X_3X_4X_5X_6X_7X_8X_9X_{10}X_{11}X_{12}X_{13}RX_{15}PX_{17}SRNX_{21}X_{22}TLTX_{26}$ (SEQ ID NO: 2) wherein $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, V, A, G or is absent, $X_8$ denotes G, A or is absent, $X_9$ denotes R or G, $X_{10}$ denotes P, A, Q or G, $X_{11}$ denotes R or K, $X_{12}$ denotes E, Q, W, A or G, $X_{13}$ denotes D or E, $X_{15}$ denotes V, L or I, $X_{17}$ denotes H or P, $X_{21}$ denotes S, T or G, $X_{22}$ denotes I or L and $X_{26}$ denotes N or H.

In certain embodiments, $X_1$ is absent, $X_2$ is absent, $X_3$ is absent, $X_4$ is absent, $X_5$ is absent and $X_6$ denotes K. In yet other embodiments, $X_1$ is absent, $X_2$ is absent, $X_3$ is absent, $X_4$ is absent, $X_5$ is absent and $X_6$ is absent.

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes P, $X_{11}$ denotes R, $X_{12}$ denotes E, $X_{13}$ denotes D, $X_{15}$ denotes V, $X_{17}$ denotes H, $X_{21}$ denotes S, $X_{22}$ denotes I and $X_{26}$ denotes N. Hence, $X_1X_2X_3X_4X_5X_6$SGRPREDRVPHSRNSITLTN (SEQ ID NO: 17). In one embodiment, X) is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{to}$ denotes P, $X_{11}$ denotes R, $X_{12}$ denotes E, $X_{13}$ denotes D, $X_{15}$ denotes V, $X_{17}$ denotes H, $X_{21}$ denotes S, $X_{22}$ denotes I and $X_{26}$ denotes N. Hence, KSGRPREDRVPHSRNSITLTN (SEQ ID NO: 18).

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes A, $X_{11}$ denotes R, $X_{12}$ denotes E, $X_{13}$ denotes D, $X_{15}$ denotes V, $X_{17}$ denotes H, $X_{21}$ denotes S, $X_{22}$ denotes I and $X_{26}$ denotes N. Hence, $X_1X_2X_3X_4X_5X_6$SGRAREDRVPHSRNSITLTN (SEQ ID NO: 19). In one embodiment, $X_1$ is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{10}$ denotes A, $X_{11}$ denotes R, $X_{12}$ denotes E, $X_{13}$ denotes D, $X_{15}$ denotes V, $X_{17}$ denotes H, $X_{21}$ denotes S, $X_{22}$ denotes I and $X_{26}$ denotes N. Hence, KSGRAREDRVPHSRNSITLTN (SEQ ID NO: 20).

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes S, $X_{22}$ denotes I and $X_{26}$ denotes N. Hence, $X_1X_2X_3X_4X_5X_6$SGRARADRVPHSRNSITLTN (SEQ ID NO: 21). In one embodiment, $X_1$ is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes S, $X_{22}$ denotes I and $X_{26}$ denotes N. Hence, KSGRARADRVPHSRNSITLTN (SEQ ID NO: 22).

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes T, $X_{22}$ denotes I and $X_{26}$ denotes N. Hence, $X_1X_2X_3X_4X_5X_6$SGRARADRVPHSRNTITLTN (SEQ ID NO: 23). In one embodiment, $X_1$ is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes T, $X_{22}$ denotes I and $X_{26}$ denotes N. Hence, KSGRARADRVPHSRNTITLTN (SEQ ID NO: 24).

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes G, $X_{11}$ denotes R, $X_{12}$ denotes G, $X_{13}$ denotes D, $X_{15}$ denotes V, $X_{17}$ denotes H, $X_{21}$ denotes G, $X_{22}$ denotes I and $X_{26}$ denotes N. Hence, $X_1X_2X_3X_4X_5X_6$SGRGRGDRVPHSRNGITLTN (SEQ ID NO: 25). In one embodiment, $X_1$ is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{10}$ denotes G, $X_{11}$ denotes R, $X_{12}$ denotes G, $X_{13}$ denotes D, $X_{15}$ denotes V, $X_{17}$ denotes H, $X_{21}$ denotes G, $X_{22}$ denotes I and $X_{26}$ denotes N. Hence, KSGRGRGDRVPHSRNGITLTN (SEQ ID NO: 26).

In one embodiment, $X_1$ denotes K or is absent, $X_2$ denotes K or is absent, $X_3$ denotes K or is absent, $X_4$ denotes K or is absent, $X_5$ denotes K or is absent, $X_6$ denotes K or is absent, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes G, $X_{22}$ denotes I and $X_{26}$ denotes N. Hence, $X_1X_2X_3X_4X_5X_6$SGRARADRVPHSRNGITLTN (SEQ ID NO: 27). In one embodiment, $X_1$ is absent, $X_2$ is absent, $X_3$ is absent, $X_4$ is absent, $X_5$ is absent, $X_6$ denotes K, $X_7$ denotes S, $X_8$ denotes G, $X_9$ denotes R, $X_{10}$ denotes A, $X_{11}$ denotes R, $X_{12}$ denotes A, $X_{13}$ denotes D, $X_{15}$ denotes V, $X_{17}$ denotes H, $X_{21}$ denotes G, $X_{22}$ denotes I and $X_{26}$ denotes N. Hence, KSGRARADRVPHSRNGITLTN (SEQ ID NO: 28).

Compounds of the present invention are useful for applications where one or more functional properties of fibronectin are desirable or where modification of one or more signaling properties associated with fibronectin are desirable. For example, compounds of the present invention may be employed as therapeutics to inhibit cell signaling. Antimetastatic effects of peptides derived from fibronectin are described for example, in Kato et al., *Clinical Cancer Research*, 8:2455-2462 (2002).

Likewise, surfaces modified using the compounds of the present invention are useful for applications where one or more functional properties of fibronectin are desirable or where modification of one or more signaling properties associated with fibronectin are desirable. Such applications include in vitro cell culture as well as fostering cell growth in vivo. For example, prosthetic devices coated with fibronectin are desirable to foster growth and migration of new epithelial tissue. Preparation of fibronectin coated prosthetic devices are well known to one of skill in the art (see, e.g., U.S. Pat. No. 5,171,318).

Surfaces modified with a compound of the present invention may employ either passive (i.e., non-covalent) coating, covalent immobilization of the compound or any other method of deposition of the compound.

Surfaces modified with a compound of the present invention for use in cell culture include cell culture vessels, cell culture devices and microcarriers. Suitable cell culture vessels for use in the present invention are well known to one of skill in the art. Examples of suitable vessels include, but are not limited to, dishes, flasks, multi-well plates, and microscopic slides, cell culture inserts. Microcarriers suitable for cell culture are also well known to one of skill in the art. See, e.g., Nie, *Biotechnol. Prog.*, 25(1):20-31 (2009).

Advantageously, cells cultured using the surfaces of the present invention are suitable for therapeutic application (e.g., in wound healing) and avoid problems inherent to the use of isolated fibronectin from a different source which may otherwise elicit an immunogenic response and even lead to rejection of transplanted cells.

EXAMPLES

The compound of the present invention having amino acid sequence KSGRPREDRVPHSRNSITLT-NSGSGSGSGSGRGDSP (SEQ ID NO: 7) was synthesized using a commercially available custom peptide synthesis service. This compound was then added on a surface to modify the surface To explore the ability of a surface modified by the compound of the present invention to mimic one or more functional characteristics of a fibronectin coated surface, cells were seeded and monitored on both such surfaces under the same culture conditions. In brief, LNCaP cells, MIA-PaCa-2, A-172, or RKO cells from ATCC were cultured according to supplier's instructions. LNCaP were cultured in RPMI-1640 Medium (ATCC Catalog No. 30-2001) supplemented with 10% fetal bovine serum. MIA-PaCa-2 and A-172 cells were grown in DMEM (Invitrogen cat #11885-084) supplemented with 10% fetal bovine serum. RKO cells were cultured in EMEM (ATCC cat#30-2003) supplemented with 10% fetal bovine serum. Cells were cultured at 37° C. in a humidified incubator with 5% $CO_2$. For seeding, media was removed, cells were washed with PBS, and 3 ml of 0.25% Trypsin-EDTA was added to the cells in T-75 flask. Flasks were examined under the microscope, once cells detached from the surface, 10 ml culture media was added to neutralize Trypsin. Cells were transferred to a 15 ml. BD Falcon tube and centrifuged at 200×g for 10 min. Supernatant was removed and the cell pellet washed once with DMEM (Invitrogen cat

11885-084) having 200 microgram/ml BSA. Cells were resuspended in DMEM having 200 microgram/ml BSA and seeded at 50,000 cells/cm² in 1.0 ml media per well of a 24 well plate. The culture surface was either a surface modified by the compound KSGRPREDRVPHSRNSITLT-NSGSGSGSGSGRGDSP (SEQ ID NO: 7) or BD BioCoat fibronectin which served as a positive control. Additionally, BD tissue culture treated surface served as negative control. Cells were incubated for 24 hr at 37° C. in a humidified incubator with 5% $CO_2$.

Figure 1:
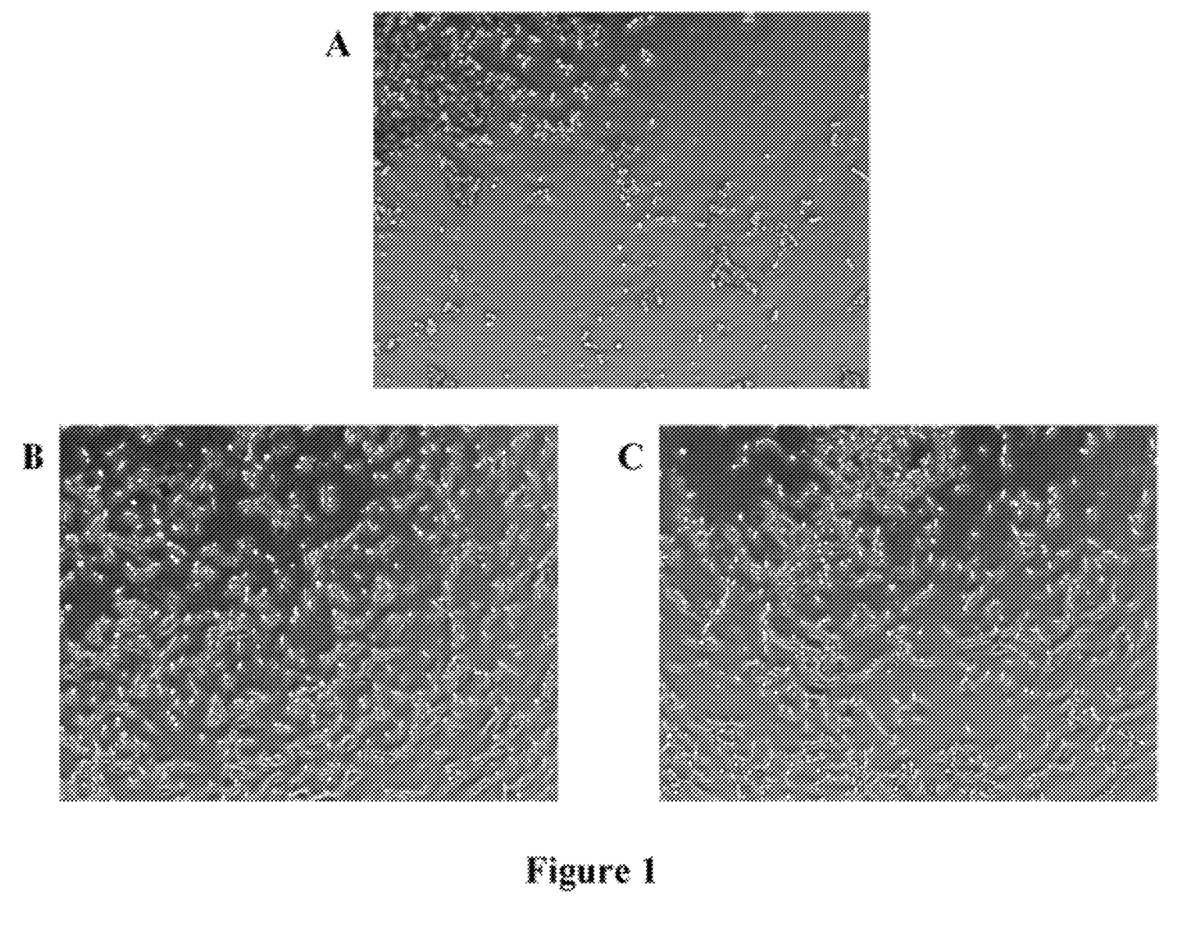
FIG. 1A is an image of LNCaP human prostate cancer cells present on a tissue culture surface without any extracellular matrix protein coating thereon.
FIG. 1B is an image of LNCaP human prostate cancer cells attached to a surface that is modified by a compound of the present invention (i.e., KSGRPREDRVPHSRNSITLTNSGSGSGSGSGRGDSP (SEQ ID NO: 7)) thereon.
FIG. 1C is an image of LNCaP human prostate cancer cells attached to a surface that has a coating of human fibronectin (i.e., BD BioCoat Fibronectin) thereon.

Following 24 hr incubation post-seeding, LNCaP cells were visualized with the aid of a microscope and images captured. Notably, cell attachment and spreading was comparable between surfaces modified by compound KSGR-PREDRVPHSRNSITLTNSGSGSGSGSGRGDSP (SEQ ID NO: 7) of the present invention (see FIG. 1B) and BD Bio-Coat fibronectin (see FIG. 1C). In contrast, cell attachment and spreading was significantly reduced in tissue culture treated surface without a coating thereon which served as a negative control (see FIG. 1A).

In addition to the aforementioned visual analysis, MTS analysis was carried out to quantify the degree of cell attachment. In brief, media was removed by inverting the plate and 300 µl complete media containing MTS (Promega cat #G3582) was added to each well of a 24 well plate. Cells were incubated for 1 hr at 37° C. in a humidified incubator at 5% $CO_2$. Following incubation, 0.1 ml media was transferred to BD Falcon™ 96 well plate and absorbance was measured at 490 nm.

Figure 2:
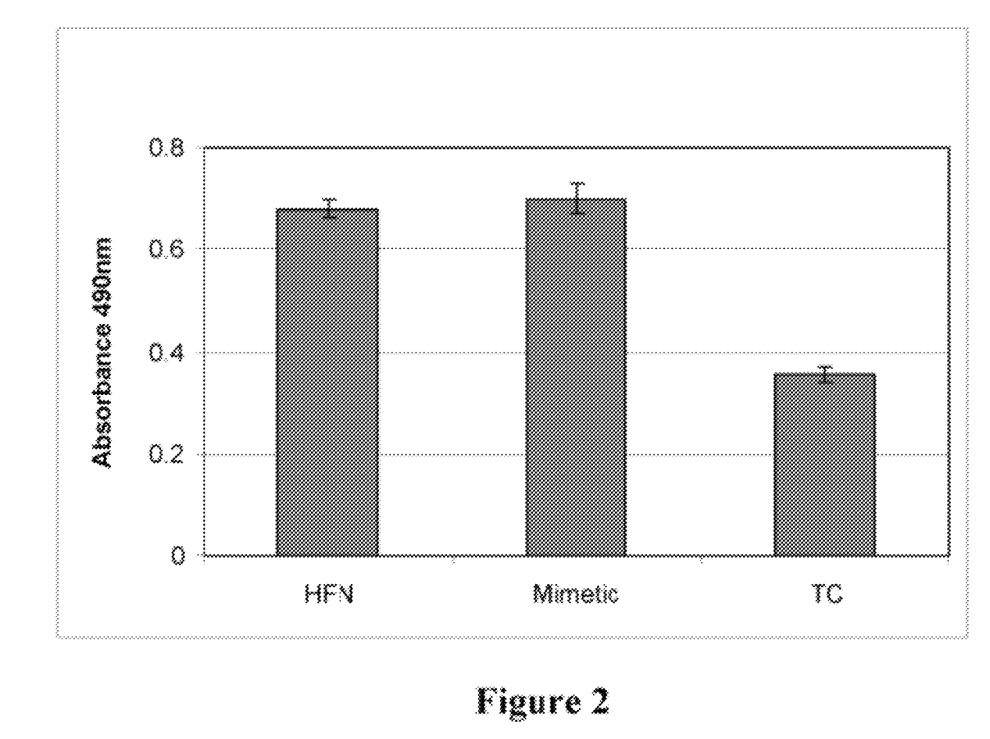
FIG. 2 is a graph illustrating the level of absorbance at 490 nm following MTS assay for quantification of LNCaP cell attachment to a BD BioCoat fibronectin surface (referred to therein as "HFN"), surface with a compound of the present invention (i.e., KSGRPREDRVPHSRNSITLTNSGSGSGSGSGRGDSP (SEQ ID NO: 7) thereon (referred to therein as "Mimetic") and control tissue culture (referred to therein as "TC") surface without any coating thereon.

As illustrated in FIG. 2, compound KSGRPREDRVPH-SRNSITLTNSGSGSGSGSGRGDSP (SEQ ID NO: 7) and BD BioCoat fibronectin treated surfaces supported comparable LNCaP cell attachment whereas LNCaP attachment to untreated tissue culture surface was significantly reduced.

Figure 3:
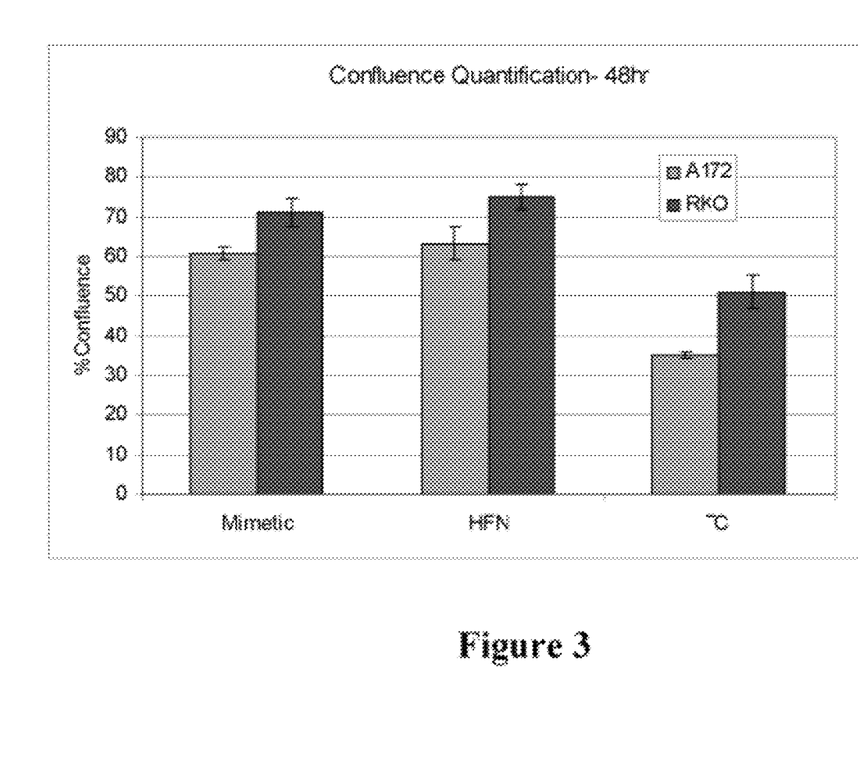
FIG. 3 is a graph illustrating the confluence quantification by IncuCyte (Essen) A-172 (of human glioblastoma cell line) and RKO (human colon carcinoma cell line) cell attachment to a BD BioCoat fibronectin surface (referred to therein as "HFN"), surface with a compound of the present invention (i.e., KSGRPREDRVPHSRNSITLTNSGSGSGSGSGRGDSP (SEQ ID NO: 7) thereon (referred to therein as "Mimetic") and control tissue culture (referred to therein as "TC") surface without any coating thereon.

Similarly, confluence quantification by IncuCyte (Essen) of A-172 and RKO cells on surfaces treated with compound KSGRPREDRVPHSRNSITLTNSGSGSGSGSGRGDSP (SEQ ID NO: 7) and BD BioCoat fibronectin were comparable (see FIG. 3). In contrast, confluence quantification to untreated tissue culture surface was significantly reduced.

Figure 4A:
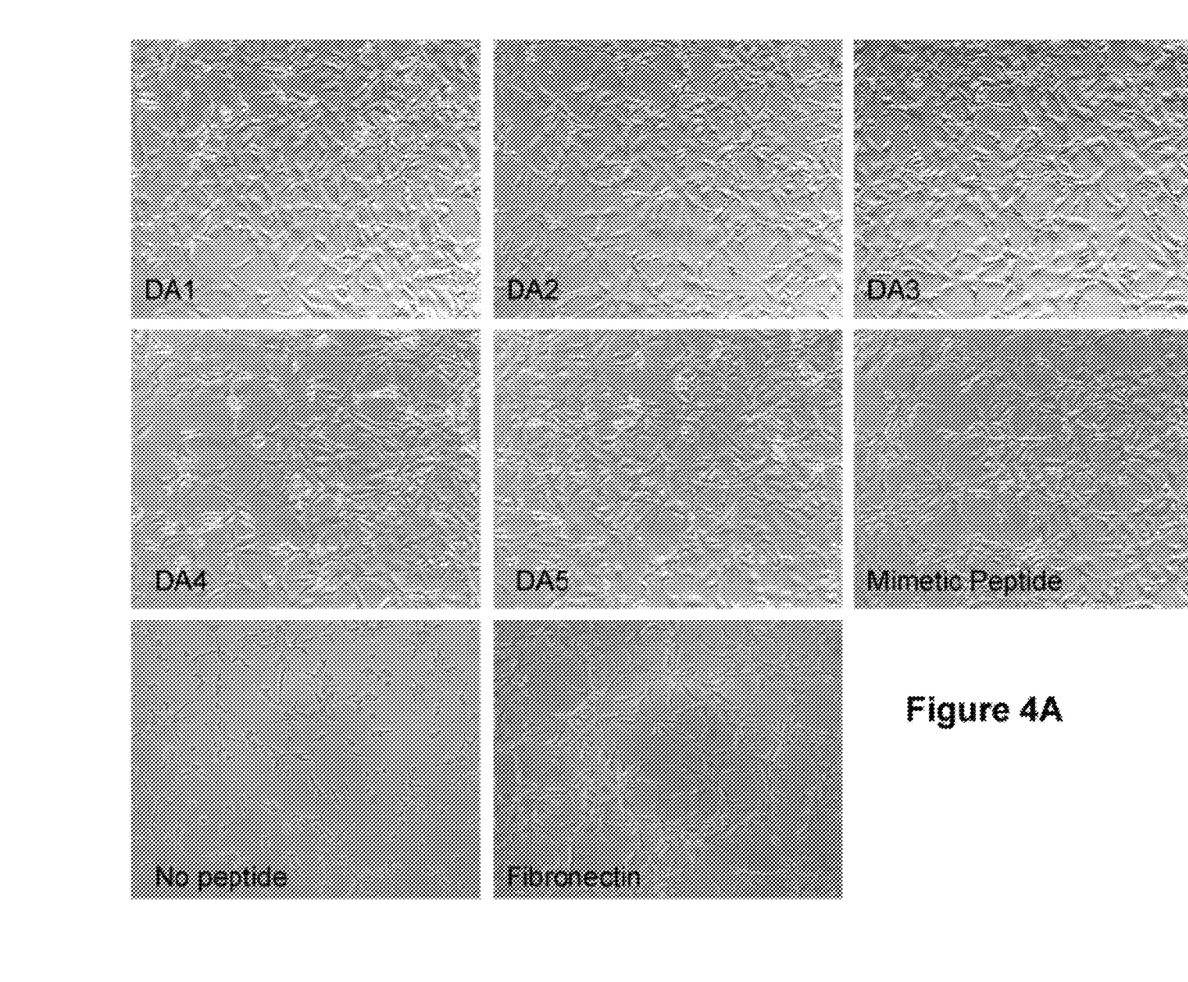
FIG. 4A is an image of A-172 human glioblastoma cancer cells attached to a surface that has a coating thereon of KSGRPREDRVPHSRNSITLTNSGTGSGTGSGRGDSP (SEQ ID NO: 8) referred to therein as "DA2", KSGRPREDRVPHSRNSITLTNGGGSGGGSGGGRGDSP (SEQ ID NO: 9) referred to therein as "DA4", KSGRARADRVPHSRNTITLTNSGSGSGSGSGRGDSP (SEQ ID NO: 10) referred to therein as "DA1", KSGRARADRVPHSRNTITLTNGGSGGSGGSGRGDSP (SEQ ID NO: 11) referred to therein as "DA3". KSGRGRGDRVPHSRNGITLTNSGSGSGSGSGRGDSP (SEQ ID NO: 12) referred to therein as "DA5", KSGRPREDRVPHSRNSITLTNSGSGSGSGSGRGDSP (SEQ ID NO: 7) referred to therein as "Mimetic Peptide", a BD BioCoat fibronectin surface referred to therein as "Fibronectin" or a surface without a peptide coating referred to therein as "No peptide." Notably, the flexible linker is underlined.
Figure 4B:
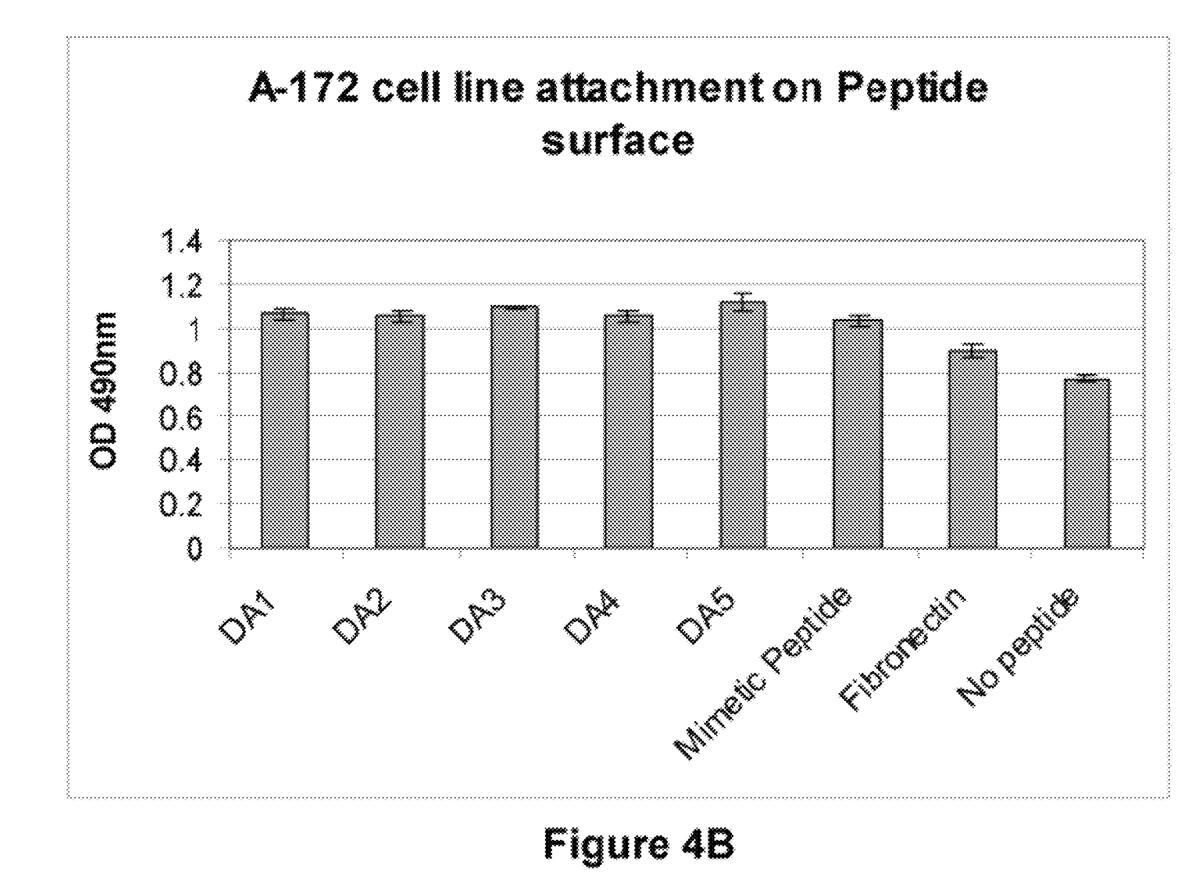

Additionally, surfaces with a coating thereon of KSGR-PREDRVPHSRNSITLTNSGSGSGSGSGRGDSP (SEQ ID NO: 7), KSGRPREDRVPHSRNSITLTNSGTGS-GTGSGRGDSP (SEQ ID NO: 8), KSGRPREDRVPHSRN-SITLTNGGGSGGGSGGGRGDSP (SEQ ID NO: 9), KSGRARADRVPHSRNTITLTNSGSGSGSGSGRGDSP (SEQ ID NO: 10), KSGRARADRVPHSRNTITLT-NGGSGGSGGGSGRGDSP (SEQ ID NO: 11), or KSGR-GRGDRVPHSRNGITLTNSGSGSGSGSGRGDSP (SEQ ID NO: 12), supported cell attachment and spreading similar to a BD BioCoat fibronectin surface (see FIG. 4A and FIG. 4B).

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A compound comprising at least two regions of a fibronectin cell-binding domain joined by a flexible linker wherein at least one region comprises amino acid sequence GRGDSP (SEQ ID NO: 1) and another region comprises $X_1X_2X_3X_4X_5X_6X_7X_8X_9X_{10}X_{11}X_{12}X_{13}RX_{15}PX_{17}SRNX_{21}X_{22}TLTX_{26}$ (SEQ ID NO: 2) wherein $X_1$ denotes K or is absent,
$X_2$ denotes K or is absent,
$X_3$ denotes K or is absent,
$X_4$ denotes K or is absent,
$X_5$ denotes K or is absent,
$X_6$ denotes K,
$X_7$ denotes S, V, A, G or is absent
$X_8$ denotes G, A or is absent
$X_9$ denotes R or G
$X_{10}$ denotes P, A, Q or G
$X_{11}$ denotes R or K
$X_{12}$ denotes E, Q, W, A or G
$X_{13}$ denotes D or E
$X_{15}$ denotes V, L or I
$X_{17}$ denotes H or P
$X_{21}$ denotes S, T or G
$X_{22}$ denotes I or L and
$X_{26}$ denotes N or H; and wherein the compound is less than 100 amino acids.

2. The compound of claim 1 wherein $X_7$ denotes S.

3. The compound of claim 2 wherein $X_8$ denotes G.

4. The compound of claim 3 wherein $X_9$ denotes R.

5. The compound of claim 1 wherein the flexible linker comprises amino acid sequence SGSGSGSGS (SEQ ID NO: 3), GGSGGSGGS (SEQ ID NO: 4), SGTGSGTGS (SEQ ID NO: 5) or GGGSGGGSGG (SEQ ID NO: 6).

6. The compound of claim 1 wherein
$X_1$ is absent,
$X_2$ is absent,
$X_3$ is absent,
$X_4$ is absent,
$X_5$ is absent,
$X_7$ denotes S
$X_8$ denotes G
$X_9$ denotes R
$X_{10}$ denotes P
$X_{11}$ denotes R
$X_{12}$ denotes E
$X_{13}$ denotes D
$X_{15}$ denotes V
$X_{17}$ denotes H
$X_{21}$ denotes S
$X_{22}$ denotes I and
$X_{26}$ denotes N.

7. The compound of claim 6 wherein the flexible linker is SGSGSGSGS (SEQ ID NO: 3).

8. A surface wherein at least a portion of the surface comprises a coating thereon of claim 1.

* * * * *

SEQUENCE LISTING

```
<160> NUMBER OF SEQ ID NOS: 28

<210> SEQ ID NO 1
<211> LENGTH: 6
<212> TYPE: PRT
<213> ORGANISM: Artificial Sequence
<220> FEATURE:
<223> OTHER INFORMATION: fibronectin cell-binding domain

<400> SEQUENCE: 1

Gly Arg Gly Asp Ser Pro
1               5

<210> SEQ ID NO 2
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
```

<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent
<220> FEATURE:
<221> NAME/KEY: misc_feature
<222> LOCATION: (7)..(7)
<223> OTHER INFORMATION: Xaa denotes S, V, A, G or is absent
<220> FEATURE:
<221> NAME/KEY: misc_feature
<222> LOCATION: (8)..(8)
<223> OTHER INFORMATION: Xaa denotes G, A or is absent
<220> FEATURE:
<221> NAME/KEY: misc_feature
<222> LOCATION: (9)..(9)
<223> OTHER INFORMATION: Xaa denotes R or G
<220> FEATURE:
<221> NAME/KEY: misc_feature
<222> LOCATION: (10)..(10)
<223> OTHER INFORMATION: Xaa denotes P, A, Q or G
<220> FEATURE:
<221> NAME/KEY: misc_feature
<222> LOCATION: (11)..(11)
<223> OTHER INFORMATION: Xaa denotes R or K
<220> FEATURE:
<221> NAME/KEY: misc_feature
<222> LOCATION: (12)..(12)
<223> OTHER INFORMATION: Xaa denotes E, Q, W, A or G
<220> FEATURE:
<221> NAME/KEY: misc_feature
<222> LOCATION: (13)..(13)
<223> OTHER INFORMATION: Xaa denotes D or E
<220> FEATURE:
<221> NAME/KEY: misc_feature
<222> LOCATION: (15)..(15)
<223> OTHER INFORMATION: Xaa denotes V, L or I
<220> FEATURE:
<221> NAME/KEY: misc_feature
<222> LOCATION: (17)..(17)
<223> OTHER INFORMATION: Xaa denotes H or P
<220> FEATURE:
<221> NAME/KEY: misc_feature
<222> LOCATION: (21)..(21)
<223> OTHER INFORMATION: Xaa denotes S, T or G
<220> FEATURE:
<221> NAME/KEY: misc_feature
<222> LOCATION: (22)..(22)
<223> OTHER INFORMATION: Xaa denotes I or L
<220> FEATURE:
<221> NAME/KEY: misc_feature
<222> LOCATION: (26)..(26)
<223> OTHER INFORMATION: Xaa denotes N or H

<400> SEQUENCE: 2

Xaa Xaa Xaa Xaa Xaa Xaa Xaa Xaa Xaa Xaa Xaa Xaa Arg Xaa Pro
1               5                   10                  15

Xaa Ser Arg Asn Xaa Xaa Thr Leu Thr Xaa
            20                  25

<210> SEQ ID NO 3
<211> LENGTH: 9
<212> TYPE: PRT
<213> ORGANISM: Artificial Sequence
<220> FEATURE:
<223> OTHER INFORMATION: flexible linker

<400> SEQUENCE: 3

Ser Gly Ser Gly Ser Gly Ser Gly Ser
1               5

<210> SEQ ID NO 4
<211> LENGTH: 9
<212> TYPE: PRT

```
<213> ORGANISM: Artificial Sequence
<220> FEATURE:
<223> OTHER INFORMATION: flexible linker

<400> SEQUENCE: 4

Gly Gly Ser Gly Gly Ser Gly Gly Ser
1               5

<210> SEQ ID NO 5
<211> LENGTH: 9
<212> TYPE: PRT
<213> ORGANISM: Artificial Sequence
<220> FEATURE:
<223> OTHER INFORMATION: flexible linker

<400> SEQUENCE: 5

Ser Gly Thr Gly Ser Gly Thr Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: flexible linker

<400> SEQUENCE: 6

Gly Gly Gly Ser Gly Gly Gly Ser Gly Gly
1               5                   10

<210> SEQ ID NO 7
<211> LENGTH: 36
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 7

Lys Ser Gly Arg Pro Arg Glu Asp Arg Val Pro His Ser Arg Asn Ser
1               5                   10                  15

Ile Thr Leu Thr Asn Ser Gly Ser Gly Ser Gly Ser Gly Ser Gly Arg
            20                  25                  30

Gly Asp Ser Pro
        35

<210> SEQ ID NO 8
<211> LENGTH: 36
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 8

Lys Ser Gly Arg Pro Arg Glu Asp Arg Val Pro His Ser Arg Asn Ser
1               5                   10                  15

Ile Thr Leu Thr Asn Ser Gly Thr Gly Ser Gly Thr Gly Ser Gly Arg
            20                  25                  30

Gly Asp Ser Pro
        35

<210> SEQ ID NO 9
<211> LENGTH: 37
<212> TYPE: PRT
```

```
<213> ORGANISM: Artificial Sequence
<220> FEATURE:
<223> OTHER INFORMATION: two regions of a fibronectin cell-binding
      domain joined by a flexible linker

<400> SEQUENCE: 9

Lys Ser Gly Arg Pro Arg Glu Asp Arg Val Pro His Ser Arg Asn Ser
1               5                   10                  15

Ile Thr Leu Thr Asn Gly Gly Gly Ser Gly Gly Gly Ser Gly Gly Gly
            20                  25                  30

Arg Gly Asp Ser Pro
            35

<210> SEQ ID NO 10
<211> LENGTH: 36
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 10

Lys Ser Gly Arg Ala Arg Ala Asp Arg Val Pro His Ser Arg Asn Thr
1               5                   10                  15

Ile Thr Leu Thr Asn Ser Gly Ser Gly Ser Gly Ser Gly Ser Gly Arg
            20                  25                  30

Gly Asp Ser Pro
            35

<210> SEQ ID NO 11
<211> LENGTH: 36
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 11

Lys Ser Gly Arg Ala Arg Ala Asp Arg Val Pro His Ser Arg Asn Thr
1               5                   10                  15

Ile Thr Leu Thr Asn Gly Gly Ser Gly Gly Ser Gly Gly Ser Gly Arg
            20                  25                  30

Gly Asp Ser Pro
            35

<210> SEQ ID NO 12
<211> LENGTH: 36
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 12

Lys Ser Gly Arg Gly Arg Gly Asp Arg Val Pro His Ser Arg Asn Gly
1               5                   10                  15

Ile Thr Leu Thr Asn Ser Gly Ser Gly Ser Gly Ser Gly Ser Gly Arg
            20                  25                  30

Gly Asp Ser Pro
            35

<210> SEQ ID NO 13
<211> LENGTH: 20
```

```
<212> TYPE: PRT
<213> ORGANISM: Artificial Sequence
<220> FEATURE:
<223> OTHER INFORMATION: two regions of a fibronectin cell-binding
      domain joined by a flexible linker

<400> SEQUENCE: 13

Ser Gly Arg Pro Arg Glu Asp Arg Val Pro His Ser Arg Asn Ser Ile
1               5                   10                  15

Thr Leu Thr Asn
            20

<210> SEQ ID NO 14
<211> LENGTH: 4
<212> TYPE: PRT
<213> ORGANISM: Artificial Sequence
<220> FEATURE:
<223> OTHER INFORMATION: linker

<400> SEQUENCE: 14

Gly Ser Gly Ser
1

<210> SEQ ID NO 15
<211> LENGTH: 10
<212> TYPE: PRT
<213> ORGANISM: Artificial Sequence
<220> FEATURE:
<223> OTHER INFORMATION: linker

<400> SEQUENCE: 15

Gly Ser Gly Ser Gly Ser Gly Ser Gly Ser
1               5                   10

<210> SEQ ID NO 16
<211> LENGTH: 6
<212> TYPE: PRT
<213> ORGANISM: Artificial Sequence
<220> FEATURE:
<223> OTHER INFORMATION: linker

<400> SEQUENCE: 16

Gly Gly Ser Gly Gly Ser
1               5

<210> SEQ ID NO 17
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
```

```
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 17

Xaa Xaa Xaa Xaa Xaa Xaa Ser Gly Arg Pro Arg Glu Asp Arg Val Pro
1               5                   10                  15

His Ser Arg Asn Ser Ile Thr Leu Thr Asn
            20                  25

<210> SEQ ID NO 18
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 18

Lys Ser Gly Arg Pro Arg Glu Asp Arg Val Pro His Ser Arg Asn Ser
1               5                   10                  15

Ile Thr Leu Thr Asn
            20

<210> SEQ ID NO 19
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 19

Xaa Xaa Xaa Xaa Xaa Xaa Ser Gly Arg Ala Arg Glu Asp Arg Val Pro
1               5                   10                  15

His Ser Arg Asn Ser Ile Thr Leu Thr Asn
            20                  25

<210> SEQ ID NO 20
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 20
```

Lys Ser Gly Arg Ala Arg Glu Asp Arg Val Pro His Ser Arg Asn Ser
1               5                   10                  15

Ile Thr Leu Thr Asn
            20

<210> SEQ ID NO 21
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 21

Xaa Xaa Xaa Xaa Xaa Xaa Ser Gly Arg Ala Arg Ala Asp Arg Val Pro
1               5                   10                  15

His Ser Arg Asn Ser Ile Thr Leu Thr Asn
            20                  25

<210> SEQ ID NO 22
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 22

Lys Ser Gly Arg Ala Arg Ala Asp Arg Val Pro His Ser Arg Asn Ser
1               5                   10                  15

Ile Thr Leu Thr Asn
            20

<210> SEQ ID NO 23
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)

```
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 23

Xaa Xaa Xaa Xaa Xaa Xaa Ser Gly Arg Ala Arg Ala Asp Arg Val Pro
1               5                   10                  15

His Ser Arg Asn Thr Ile Thr Leu Thr Asn
            20                  25

<210> SEQ ID NO 24
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 24

Lys Ser Gly Arg Ala Arg Ala Asp Arg Val Pro His Ser Arg Asn Thr
1               5                   10                  15

Ile Thr Leu Thr Asn
            20

<210> SEQ ID NO 25
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 25

Xaa Xaa Xaa Xaa Xaa Xaa Ser Gly Arg Gly Arg Gly Asp Arg Val Pro
1               5                   10                  15
```

His Ser Arg Asn Gly Ile Thr Leu Thr Asn
            20                  25

<210> SEQ ID NO 26
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 26

Lys Ser Gly Arg Gly Arg Gly Asp Arg Val Pro His Ser Arg Asn Gly
1               5                   10                  15

Ile Thr Leu Thr Asn
            20

<210> SEQ ID NO 27
<211> LENGTH: 26
<212> TYPE: PRT
<213> ORGANISM: Artificial Sequence
<220> FEATURE:
<223> OTHER INFORMATION: fibronectin cell-binding domain
<220> FEATURE:
<221> NAME/KEY: misc_feature
<222> LOCATION: (1)..(1)
<223> OTHER INFORMATION: Xaa denotes K or is absent
<220> FEATURE:
<221> NAME/KEY: misc_feature
<222> LOCATION: (2)..(2)
<223> OTHER INFORMATION: Xaa denotes K or is absent
<220> FEATURE:
<221> NAME/KEY: misc_feature
<222> LOCATION: (3)..(3)
<223> OTHER INFORMATION: Xaa denotes K or is absent
<220> FEATURE:
<221> NAME/KEY: misc_feature
<222> LOCATION: (4)..(4)
<223> OTHER INFORMATION: Xaa denotes K or is absent
<220> FEATURE:
<221> NAME/KEY: misc_feature
<222> LOCATION: (5)..(5)
<223> OTHER INFORMATION: Xaa denotes K or is absent
<220> FEATURE:
<221> NAME/KEY: misc_feature
<222> LOCATION: (6)..(6)
<223> OTHER INFORMATION: Xaa denotes K or is absent

<400> SEQUENCE: 27

Xaa Xaa Xaa Xaa Xaa Xaa Ser Gly Arg Ala Arg Ala Asp Arg Val Pro
1               5                   10                  15

His Ser Arg Asn Gly Ile Thr Leu Thr Asn
            20                  25

<210> SEQ ID NO 28
<211> LENGTH: 21
<212> TYPE: PRT
<213> ORGANISM: Artificial Sequence
<220> FEATURE:
<223> OTHER INFORMATION: fibronectin cell-binding domain

<400> SEQUENCE: 28

Lys Ser Gly Arg Ala Arg Ala Asp Arg Val Pro His Ser Arg Asn Gly
1               5                   10                  15

Ile Thr Leu Thr Asn
            20